US005543133A

United States Patent [19]
Swanson et al.

[11] Patent Number: 5,543,133
[45] Date of Patent: Aug. 6, 1996

[54] PROCESS OF PREPARING X-RAY CONTRAST COMPOSITIONS CONTAINING NANOPARTICLES

[75] Inventors: Jon R. Swanson, Macungie; H. William Bosch, Bryn Mawr; Kathleen J. Illig, Phoenixville; Donna M. Marcera, Collegeville; Ronald L. Mueller, Downingtown, all of Pa.

[73] Assignee: NanoSystems L.L.C., Collegeville, Pa.

[21] Appl. No.: 388,099

[22] Filed: Feb. 14, 1995

[51] Int. Cl.$^6$ .................... A61K 49/00; A61K 49/04
[52] U.S. Cl. .................... 424/9.45; 424/9.451
[58] Field of Search .................... 424/9.45, 9.451

[56] References Cited

U.S. PATENT DOCUMENTS

| | | | |
|---|---|---|---|
| 4,107,288 | 8/1978 | Oppenheim et al. | 424/22 |
| 4,250,113 | 2/1981 | Nordal et al. | 564/153 |
| 4,396,598 | 8/1983 | Lin | 424/5 |
| 4,540,602 | 9/1985 | Motoyama et al. | 427/213.31 |
| 4,826,686 | 5/1989 | Violanto et al. | 424/489 |
| 5,039,527 | 8/1991 | Tabibi et al. | 424/450 |
| 5,118,528 | 6/1992 | Fessi et al. | 427/213.36 |
| 5,145,684 | 9/1992 | Liversidge et al. | 424/489 |
| 5,228,905 | 7/1993 | Grunewalder et al. | 106/2 |
| 5,233,995 | 8/1993 | Yunelson et al. | 128/662.02 |
| 5,318,767 | 6/1994 | Liversidge et al. | 424/4 |
| 5,342,609 | 8/1994 | Meeh et al. | 424/9 |

FOREIGN PATENT DOCUMENTS

| | | |
|---|---|---|
| 0498482 | 8/1992 | European Pat. Off. |
| WO90/07491 | 7/1990 | WIPO. |

OTHER PUBLICATIONS

Swanson et al, "Pharmaceuticals in Medical Imaging," 1990.
Violante and Fioclan, "Handbook of Experimental Pharmacology", vol. 73, chapter 13. (1990).
Lachman et al, "The Theory and Practice of Industrial Pharmacology", Chapter 2, Milling, p. 45 (1986).
Gregoriadis, Da Silva and Florence, "A Procedure for the Efficient Entrapment of Drugs in Dehydration–Rehydreation Liposomes (DRVs)", In. J. Pharm. 65, 235–242 (1990).
Doegito et al, "New Techniques for Preparing Submicronic Emulsion . . . Application to Amphoteric–B" STP Pharma Sciences 4, 155–162 (1994).
Lidgate, et al, "Formulation of Vaccine Adjuvant Muramyl-dipeptides Part 3. Processing Optimization, Characterization as Bioactivity of an Emulsion Vehicle", Pharm. Res. 6, 748–752 (1989).
Talsman et al, "The Size Reduction of Liposomes with a High Pressure Homogenizer (microfluidizer)", Drug Dev. Ind. Pharm. 15, 197–207, (1989).
Lidgate, et al, "Sterile Filtration of a Parenteral Emulsion", Pharm. Res. 9, 860–863 (1990).
Bodmeier and Chen, "Indomethacin Polymeric Nanosuspensions Prepared by Microfluidization" J. Contr. Rel. 12, 223–233 (1990).
Bodmeier et al, "Spontaneous Formation of Drugs Containing Acrylic Nanoparticles," J. Microencap, 8, 161–170 (1991).
Koosha and Muller, "Nanoparticle Production by Microfluidization", Archiv. Dev. Parmazie. 321, 680 (1989).
Investigative Radiology, vol. 19, Jul.–Aug., 1984.
Radiology, 142; 115–119, Jan. 1982.
Handbook of Pharmaceutical Excipients, 1986.

*Primary Examiner*—Richard L. Raymond
*Assistant Examiner*—Mary C. Cebulak
*Attorney, Agent, or Firm*—Rudman & Balogh

[57] ABSTRACT

A process of preparing nanoparticulate contrast agents comprising the steps of:
  preparing a premix of the contrast agent and a surface modifier; and
  subjecting the premix to mechanical means to reduce the particle size of the contrast agent, the mechanical means producing shear, impact, cavitation and attrition.

22 Claims, No Drawings

PROCESS OF PREPARING X-RAY CONTRAST COMPOSITIONS CONTAINING NANOPARTICLES

BACKGROUND OF THE INVENTION

1. Field of the Invention

This invention relates to a process for preparing x-ray contrast compositions containing radiopaque nanoparticles.

2. Reported Developments

X-Ray imaging is a well known and extremely valuable tool for the early detection and diagnosis of various disease states in the human body. The use of contrast agents for image enhancement in medical x-ray imaging procedures is widespread. An excellent background on contrast agents and media in medical imaging is provided by D. P. Swanson et al., *Pharmaceuticals in Medical Imaging*, 1990, MacMillan Publishing Company, the disclosure of which is hereby incorporated by reference in its entirety.

Briefly, in x-ray imaging, transmitted radiation is used to produce a radiograph based upon overall tissue attenuation characteristics. X-rays pass through various tissues and are attenuated by scattering, i.e., reflection or refraction or energy absorption. However, certain body organs, vessels and anatomical sites exhibit so little absorption of x-ray radiation that radiographs of these body portions are difficult to obtain. To overcome this problem, radiologists routinely introduce an x-ray absorbing medium containing a contrast agent into such body organs, vessels and anatomical sites.

Currently available x-ray contrast agents generally exhibit a lack of site directed delivery or compartmentalization. Consequently, large quantities of agent are normally required for imaging. It would be desirable to restrict the contrast agent to specific biological or anatomical compartments, such as the blood pool, liver, kidney or spleen. This would reduce the overall amount of agent which needs to be administered to achieve the desired contrast enhancement.

Maximum enhancement of major blood vessels takes place during the so-called vascular phase of contrast media kinetics which occurs within about the first two minutes following the intravascular infusion or bolus injection of the contrast media. This is because the plasma concentration of an intravascular contrast medium decreases rapidly as a result of vascular mixing transcapillary diffusion of the medium from the circulation into the interstitial spaces and renal excretion. Consequently, imaging of blood vessels must take place within a narrow time window, typically within a few minutes after infusion or injection of the x-ray contrast agent. Currently, there is no commercially available x-ray contrast agent for imaging blood vessels which provides good contrast images of the vasculature for an extended period of time. Therefore, multiple injections are often required to visualize the vasculature adequately. Furthermore, arteriography, as currently practiced, typically requires percutaneous or surgical catheterization, fluoroscopic localization and multiple bolus arterial administrations to adequately visualize a given vascular region.

The need for improved visualization of the liver, kidney and spleen, particularly for early detection of metastases, has led to numerous attempts at developing a contrast medium for accumulation by the mononuclear phagocyte system (MPS). In *Handbook of Experimental Pharmacology*, Vol. 73, Radiocontrast Agents, Chapter 13, "Particulate Suspensions as Contrast Media", Violante and Fischer describe and analyze the problems and complexities involved in designing and formulating such a medium. Inasmuch as the MPS of the liver and spleen is known to trap particles by phagocytosis, contrast agents in particulate form, such as emulsions of iodinated oils, e.g., iodinated ethyl esters of poppy seed oil, and liposomes containing water-soluble iodinated contrast agents have been proposed for liver and spleen visualization. However, emulsions tend to be unacceptably toxic when administered both intravenously and subcutaneously and liposomes tend to require unacceptably large amounts of lipid to achieve adequate contrast enhancement. The MPS or Kuppfer cells of the liver, to which liposomes and emulsions have been directed, constitute approximately 5 percent of the total cell population, the remainder being hepatocyte cells.

Submicron inorganic radioactive thorium dioxide particles have been used for liver visualization and have shown effective contrast enhancement in clinical testing. However, their use has been discontinued because of the extremely lengthy retention of the particles in e liver. This, in combination with the inherent radioactivity of thorium, has led to serious adverse side effects including neoplasm and fibrosis.

Violante et al, U.S. Pat. No. 4,826,689, disclose a method of making uniformly sized noncrystalline amorphous particles from water-insoluble organic compounds wherein the organic compound is dissolved in an organic solvent. In one embodiment, iodipamide ethyl ester is dissolved in dimethylsulfoxide. However solvent precipitation techniques such as described in U.S. Pat. No. 4,826,689 for preparing particles tend to provide solvent contaminated particles. Such solvents are often toxic and can be very difficult, if not impossible, to adequately remove to pharmaceutically acceptable levels for diagnostic imaging. Additionally, amorphous materials and formulations tend to exhibit unacceptably poor stability and/or short shelf-lives.

Motoyama et al, U.S. Pat. No. 4,540,602 disclose that a solid drug can be pulverized in an aqueous solution of a water-soluble high molecular substance, and that as a result of such wet grinding, the drug is formed into finely divided particles ranging from 0.5 μm or less to 5 μm in diameter. However, there is no suggestion that particles having an average particle size of less than about 400 nm can be obtained. Indeed, attempts to reproduce the wet grinding procedures described by Motoyama et al resulted in particles having an average particle size of much greater than 1 μm.

PCT/EP90/00053 describes water-insoluble iodinated carbonate esters reported to be useful as contrast agents for visualization of the liver and spleen. Particles of mean diameter on the order of 1.0 micron of the disclosed esters reportedly are taken up by the reticuloendothelial system of the liver and spleen. However, such particles are prepared by conventional mechanical crushing or spray drying techniques or by solvent precipitation techniques such as described in U.S. Pat. No. 4,826,689.

Recently, the prior art has reported production and utilization of nanoparticulate crystalline substances found to be desirable in both pharmaceutical compositions for prevention and treatment of diseases and radiopaque compositions for detection of abnormalities in soft tissues used in conjunction with radiographic examinations.

Methods of making finely divided drugs have been studied and efforts have been made to control the size and size range of drug particles in pharmaceutical compositions. For example, dry milling techniques have been used to reduce particle size and hence influence drug absorption. However, in conventional dry milling, as discussed by Lachman, et al., *The Theory and Practice of Industrial Pharmacy*, Chapter 2, "Milling", p.45 (1986), the limit of fineness is reached in the region of 100 microns (100,000 nm) when material cakes on the milling chamber. Lachman, et al. note that wet grinding is beneficial in further reducing particle size, but that flocculation restricts the lower particle size limit to approximately 10 microns (10,000 nm). However, there tends to be a bias in the pharmaceutical art against wet milling due to concerns associated with contamination. Commercial airjet milling techniques have provided particles ranging in average particle size from as low as about 1 to 50 μm (1,000–50,000 nm).

Other techniques for preparing pharmaceutical compositions include loading drugs into liposomes or polymers, e.g., during emulsion polymerization. However, such techniques have problems and limitations. For example, a lipid soluble drug is often required in preparing suitable liposomes. Further, unacceptably large amounts of the liposome or polymer are often required to prepare unit drug doses. Further still, techniques for preparing such pharmaceutical compositions tend to be complex. A principal technical difficulty encountered with emulsion polymerization is the removal of contaminants, such as unreacted monomer or initiator, which can be toxic, at the end of the manufacturing process.

EPO 275,796 describes the production of colloidally dispersible systems comprising a substance in the form of spherical particles smaller than 500 nm. However, the method involves a precipitation effected by mixing a solution of the substance and a miscible non-solvent for the substance and results in the formation of non-crystalline nanoparticles. Furthermore, precipitation techniques for preparing particles tend to provide particles contaminated with solvents. Such solvents are often toxic and can be very difficult, if not impossible, to adequately remove to pharmaceutically acceptable levels to be practical.

U.S. Pat. No. 4,107,288 describes particles in the size range from 10 to 1,000 nm containing a biologically or pharmacodynamically active material. However, the particles comprise a crosslinked matrix of macromolecules having the active material supported on or incorporated into the matrix.

U.S. Pat. No. 5,145,684 discloses a process for preparing particles consisting of a crystalline drug substance having a surface modifier or surface active agent adsorbed on the surface of the particles in an amount sufficient to maintain an average particle size of less than about 400 manometers. The process of preparation comprises the steps of dispersing the drug substance in a liquid dispersion medium and applying mechanical means in the presence of grinding media to reduce the particle size of the drug substance to an average particle size of less than 400 nm. The particles can be reduced in the presence of a surface active agent or, alternatively, the particles can be contacted with a surface active agent after attrition. The presence of the surface active agent prevents flocculation/agglomeration of the nanoparticles.

The mechanical means applied to reduce the particle size of the drug substance is a dispersion mill, the variety of which include a ball mill, an attrition mill, a vibratory mill and media mill, such as sand mill, and a bead mill.

The grinding media for the particle size reduction is spherical or particulate in form and includes: $ZrO_2$ stabilized with magnesia, zirconium silicate, glass, stainless steel, titania, alumina and $ZrO_2$ stabilized with yttrium. Processing time of the sample can be several days long. This patent is incorporated herein in its entirety by reference.

To a more limited extent the prior art also utilized microfluidizers for preparing small particle-size materials in general. Microfluidizers are relatively new devices operating on the submerged jet principle. In operating a microfluidizer to obtain nanoparticulates, a premix flow is forced by a high pressure pump through a so-called interaction chamber consisting of a system of channels in a ceramic block which split the premix into two streams. Precisely controlled shear, turbulent and cavitational forces are generated within the interaction chamber during microfluidization. The two streams are recombined at high velocity to produce droplet shear. The so-obtained product can be recycled into the microfluidizer to obtain smaller and smaller particles.

The prior art has reported two distinct advantages of microfluidization over conventional milling processes (such as reported in U.S. Pat. No. 5,145,684, supra): substantial reduction of contamination of the final product, and the ease of production scaleup.

Numerous publications and patents were devoted to emulsions, liposomes and/or microencapsulated suspensions of various substances including drug substances produced by the use of microfluidizers. See, for example:

1) U.S. Pat. No. 5,342,609, directed to methods of preparing solid apatite particles used in magnetic resonance imaging, x-ray and ultrasound.

2) U.S. Pat. No. 5,228,905, directed to producing an oil-in-water dispersion for coating a porous substrate, such as wood.

3) U.S. Pat. No. 5,039,527 is drawn to a process of producing hexamethylmelamine containing parenteral emulsions.

4) G. Gregoriadis, H. Da Silva, and A. T. Florence, "A Procedure for the Efficient Entrapment of Drugs in Dehydration-Rehydration Liposomes (DRVs)," *Int. J. Pharm.* 65, 235–242 (1990).

5) E. Doegito, H. Fessi, M. Appel, F. Puisieux, J. Bolard, and J. P. Devissaguet, "New Techniques for Preparing Submicronic Emulsions—Application to Amphotericine-B,: *STP Pharma Sciences* 4, 155–162 (1994).

6) D. M. Lidgate, R. C. Fu, N. E. Byars, L. C. Foster, and J. S. Fleitman, "Formulation of Vaccine Adjuvant Muramyldipeptides. Part 3. Processing Optimization, Characterization and Bioactivity of an Emulsion Vehicle," *Pharm Res.* 6, 748–752 (1989).

7) H. Talsma, A. Y. Ozer, L. VanBloois, and D. J. Crommelin, "The Size Reduction of Liposomes with a High Pressure Homogenizer (Microfluidizer): Characterization of Prepared Dispersions and Comparison with Conventional Methods," *Drug Dev. Ind. Pharm.* 15, 197–207 (1989).

8) D. M. Lidgate, T. Trattner, R. M. Shultz, and R. Maskiewicz, "Sterile Filtration of a Parenteral Emulsion," *Pharm. Res.* 9, 860–863 (1990).

9) R. Bodmeier, and H. Chen, "Indomethacin Polymeric Nanosuspensions Prepared by Microfluidization," *J. Contr. Rel.* 12, 223–233 (1990).

10) R. Bodmeier, H. Chen, P. Tyle, and P. Jarosz, "Spontaneous Formation of Drug-Containing Acrylic Nanoparticles," *J. Microencap*, 8, 161–170 (1991).

11) F. Koosha, and R. H. Muller, "Nanoparticle Production by Microfluidization," *Archiv DerPharmazie* 321, 680 (1988).

However, reports are few on reducing mean particle size (hereinafter sometimes abbreviated as MPS) of water-insoluble materials for use in pharmaceutical/diagnostic imaging compositions.

The present invention is directed to a process incorporating the advantages of microfluidizer process over conventional milling processes along with utilizing formulation and/or process parameters necessary for successful particle size reduction of a pharmaceutical suspension for x-ray contrast use prepared by microfluidization.

The primary forces attributed to microfluidization for producing either emulsions or dispersions, and for reducing the MPS of water-insoluble materials include: shear, involving boundary layers, turbulent flow, acceleration and change in flow direction; impact, involving collision of solid elements and collision of particles in the chamber of microfluidizer; and cavitation, involving an increased change in velocity with a decreased change in pressure and turbulent flow. An additional force can be attributed to conventional milling processes of attrition, i.e., grinding by friction. In reference to conventional milling process it is understood that the process involves the use of gravity, attrition and/or media mills, all containing a grinding media.

SUMMARY OF THE INVENTION

In accordance with the present invention, there is provided a process of preparing stable, dispersible water-insoluble, radiopaque nanoparticles consisting essentially of an x-ray contrast substance having a surface modifier adsorbed on the surface thereon comprising the steps of:

a) dispersing an x-ray contrast substance in a liquid dispersion medium containing a surface modifier; and b) subjecting the liquid dispersion medium to the comminuting action of a microfluidizer asserting shear, impact and cavitation forces onto the x-ray contrast substance contained in the liquid dispersion medium for a time necessary to reduce the mean particle size of said x-ray contrast substance to less than 400 nm.

We have discovered that surface modified crystalline nanoparticles of water-insoluble x-ray contrast agents prepared by the process of the present invention provide images of exceptional resolution and can be formulated for enhanced delivery to specific tissue or fluid sites, e.g., the blood pool, liver, kidney, bone marrow, lymph nodes and spleen. Moreover, preferred x-ray contrast agents when administered intravenously provide effective imaging of the blood pool within the vascular system for remarkably long periods of time.

More particularly, in accordance with this invention, there is provided an x-ray contrast composition comprising particles prepared by the process of the present invention consisting essentially of a non-radioactive crystalline organic x-ray contrast agent having a surface modifier adsorbed on the surface thereof in an amount sufficient to maintain an effective average particle size of less than 400 nm, and a pharmaceutically acceptable carrier therefor.

In accordance with the invention there is also provided a method for x-ray diagnostic imaging which comprises administering to a patient an effective contrast producing amount of a composition prepared by the process of the present invention.

DETAILED DESCRIPTION OF THE INVENTION

The Contrast Agent

The x-ray contrast composition of this invention comprises particles of an organic x-ray contrast agent having a surface modifier adsorbed on the surface thereof in an amount sufficient to maintain an effective average particle size of less than 400 nm. Such particles are disclosed in U.S. Pat. No. 5,318,767, which is incorporated herein by reference.

The x-ray contrast agent useful in the practice of this invention is non-radioactive and exists as a discrete, crystalline phase of an organic substance. The crystalline phase differs from an amorphous or non-crystalline phase which results from solvent precipitation techniques such as described in U.S. Pat. No. 4,826,689 noted above. The organic substance can be present in one or more suitable crystalline phases. The invention can be practiced with a wide variety of crystalline, non-radioactive x-ray contrast agents. However, the x-ray contrast agent must be poorly soluble and dispersible in at least one liquid medium. By "poorly soluble", it is meant that the agent has a solubility in the liquid dispersion medium, e.g., water, of less than about 10 mg/ml, and preferably of less than about 1 mg/ml. The preferred liquid dispersion medium is water. Additionally, the invention can be practiced with other liquid media in which the selected x-ray contrast agent is poorly soluble and dispersible, including, for example, aqueous saline solutions, such as phosphate buffered saline (PBS), plasma, mixed aqueous and nonaqueous solutions, for example, water and alcohol, and suitable nonaqueous solvents such as alcohol, glycerol and the like.

The x-ray contrast agent can be an iodinated compound. The iodinated compound can be aromatic or nonaromatic. Aromatic compounds are preferred. The iodinated compound can comprise, one, two, three or more iodine atoms per molecule. Preferred species contain at least two, and more preferably, at least three iodine atoms per molecule. The iodinated compounds selected can contain substituents that do not impart solubility to the compound, such as, for example, alkylureido, alkoxyacylamido, hydroxyacetamido, butyrolactamido, succinimido, trifluoroacetamido, carboxy, carboxamido, hydroxy, alkoxy, acylamino, and the like substituents.

A preferred class of contrast agents includes various esters and amides of iodinated aromatic acids. The esters preferably are alkyl or substituted alkyl esters. The amides can be primary or secondary amides, preferably alkyl or substituted alkyl amides. For example, the contrast agent can be an ester or amide of a substituted triiodobenzoic acid such as an acyl, carbamyl, and/or acylmethyl substituted triiodobenzoic acid. Illustrative representative examples of iodinated aromatic acids include, but are not limited to, diatrizoic acid, metrizoic acid, iothalamic acid, trimesic acid, ioxaglic acid (hexabrix), ioxitalamic acid, tetraiodoterephthalic acid, and the like. It is contemplated that poorly soluble derivatives of iodamide and iopyrol can be used herein.

The invention can also be practiced with poorly soluble derivatives, e.g., ester and ether derivatives, of hydroxylated nonionic x-ray contrast agents. Illustrative nonionic contrast agents include, but are not limited to, metrizamide; ioglunide; iopamidol; iopromide; iogulamide; iohexol, and other compounds described in U.S. Pat. No. 4,250,113; Ioversol, and other compounds described in U.S. Pat. No. 4,396,598; nonionic triiodinated compounds, such as described in investigative Radiology, Vo. 19, July–August 1984; and nonionic dimers, such as described in Radiology, 142:115–118, January 1982. The invention can be practiced with poorly soluble derivatives of iodomethane sulfonamides, iodinated aromatic glucoanilides, 2-ketogulonamides, reversed amides, peptides, carbamates, esters, glycoside and glucose derivatives, benzamide derivatives, isophthalamides, bis compounds, and bispolyhydroxylated acylamides, such as described in Volume 73 of the Handbook of Experimental Pharmacology, entitled Radiocontrast Agents, edited by M. Sovak, 1984, Springer-Verlag, Berlin, pages 56–73.

Many of the iodinated molecules described above, if in monomeric form, can also be prepared as dimers (sometimes referred to as bis compounds), trimers (sometimes referred to as tris compounds), etc., by techniques known in the art. It is contemplated that this invention can be practiced with poorly soluble-iodinated compounds in monimeric, dimeric, trimeric and polymeric forms. Representative illustrative compounds are described by Sovak, cited above, pages 40–53.

Classes of preferred contrast agents have the following structural formulae:

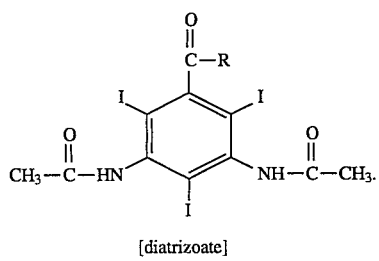

[diatrizoate]    A

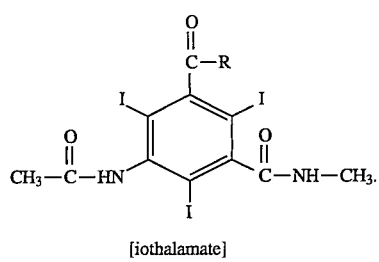

[iothalamate]    B

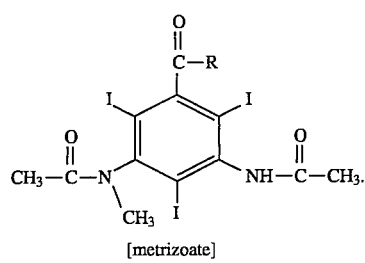

[metrizoate]    C

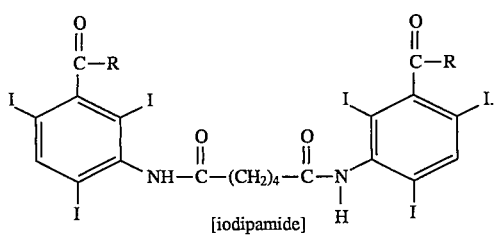

[iodipamide]    D

In the above structures, R can be OR$^1$, N$\begin{smallmatrix}R^2\\R^3\end{smallmatrix}$, alkylene-C(=O)-OR$^1$, or -O-alkylene-C(=O)-OR$^1$;

wherein R$^1$ is alkyl, and R$^2$ and R$^3$ are independently H or alkyl.

Each alkyl group can independently contain from 1–20, preferable 1–8, and more preferably, 1–4 carbon atoms. The alkylene group preferably contains from 1 to 4 carbon atoms such as methylene, ethylene, propylene and the like.

Particularly preferred contrast agents include the ethyl ester of diatrizoic acid, i.e., ethyl-3,5-diacetamido-2,4,6-triiodobenzoate, also known as ethyl-3,5-bis (acetylamino)-2,4,6-triodobenzoate or ethyl diatrizoate, having the structural formula A above wherein R=—OCH$_2$CH$_3$(WIN 8883); the ethyl glycolate ester of diatrizoic acid, i.e., ethyl (3, 5-bis (acetylamino)-2,4,6-triiodobenzoyloxy) acetate, also known as ethyl diatrizoxyacetate, having the structural formula A above wherein

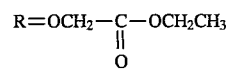

(WIN 12901); and ethyl-2-(3,5-bis(acetylamino) -2,4,6-triiodobenzoyloxy)butyrate, also known as ethyl-2-diatrizoxybutyrate (WIN 16318).

In addition, it is expected that the invention can be practiced in conjunction with the water-insoluble iodinated carbonate esters described in PCT/EP90/00053.

The above described x-ray contrast agents are known compounds and/or can be prepared by techniques known in the art. For example, water-insoluble esters and terminal amides of acids such as the above-described iodinated aromatic acids can be prepared by conventional alkylation or amidation techniques known in the art. The above-noted acids and other acids which can be used as starting materials are commercially available and/or can be prepared by techniques known in the art.

Surface Modifiers

The particles useful in the practice of this invention include a surface modifier. Surface modifiers useful herein physically adhere to the surface of the x-ray contrast agent but do not chemically react with the agent or itself. Individually adsorbed molecules of the surface modifier are essentially of intermolecular crosslinkages. Suitable surface modifiers can be selected from known organic and inorganic pharmaceutical excipients such as various polymers, low-molecular weight oligomers, natural products and surfactants. Preferred surface modifiers include nonionic and anionic surfactants. Representative examples of surface modifiers include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxymethylcellulose, hydroxypropylcellulose, hydroxypropylmethylcellulose phthalate, noncrystalline cellulose, magnesium aluminum silicate, triethanolamine, polyvinyl alcohol, and polyvinylpyrrolidone (PVP). Most of these surface modifiers are known pharmaceutical excipients and are described in detail in the *Handbook of Pharmaceutical Excipients*, published jointly by the American Pharmaceutical Association and The Pharmaceutical Society of Great Britain, the Pharmaceutical Press, 1986, the disclosure of which is hereby incorporated by reference in its entirety.

Particularly preferred surface modifiers include polyvinylpyrrolidone, tyloxapol, poloxamers such as Pluronic F68 and F108, which are block copolymers of ethylene oxide and propylene oxide, and poloxamines such as Tetronic 908 (also known as Poloxamine 908), which is a tetrafunctional block copolymer derived from sequential addition of propylene oxide and ethylene oxide to ethylenediamine, available from BASF. dextran, lecithin, dialkylesters of sodium sulfosuccinic acid, such as Aerosol OT, which is a dioctyl ester of sodium sulfosuccinic acid, available from American Cyanamid, Duponol P, which is a sodium lauryl sulfate, available from DuPont, Triton X-200, which is an alkylaryl polyether sulfonate, available from Rohm and Haas, Tween 80, which is a polyoxyethylene sorbitan fatty acid ester, available from ICI Speciality Chemicals, and Carbowax 3350 and 934, which are polyethylene glycols available from Union Carbide. Surface modifiers which have been found to be particularly useful include Tetronic 908, the Tweens, Pluronic F68 and polyvinylpyrrolidone. Other useful surface modifiers include:

decanoyl-N-methylglucamide;
n-decyl β-D-glucopyranoside;
n-decyl β-D-maltopyranoside;
n-dodecyl β-D-glucopyranoside;
n-dodecyl β-maltoside;
heptanoyl-N-methylglucamide
n-heptyl β-D-glucopyranoside;
n-heptyl β-D-thioglucoside;
n-hexyl β-D-glucopyranoside;
nonanoyl-N-methylglucamide;
n-nonyl β-D-glucopyranoside;
octanoyl-N-methylglucamide;
n-octyl β-D-glucopyranoside;
octyl β-D-thioglucopyranoside and the like.

A particularly preferred class of surface modifiers includes water-soluble or water-dispersible compounds having the formula

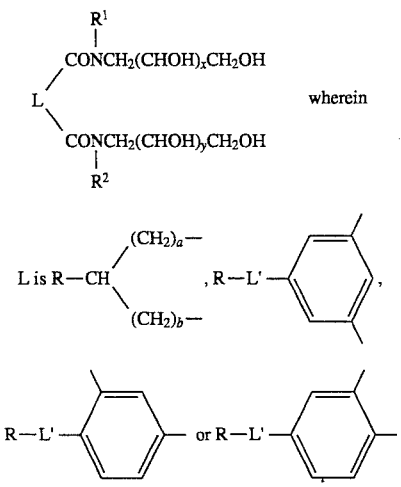

L' is a chemical bond, —O—, —S—, —NH—, —CONH— or —SO$_2$NH—; R is a hydrophobic substituted or unsubstituted alkyl, substituted or unsubstituted cycloalkyl, or a substituted or unsubstituted aryl group;

each of R$^1$ and R$^2$ independently is hydrogen or an alkyl group having from 1 to 4 carbon atoms;

each of a and b independently is 0 or an integer from 1 to 3, provided that the sum of a and b is not greater than 3; and, each of x and y independently is an integer from 3 to 7.

Preferred compounds within this class conform to the above structure wherein R contains from 6 to 36 carbon atoms, for example, R is an n-alkyl group containing from 6 to 18 carbon atoms, each of R$^1$ and R$^2$ independently is a methyl, ethyl, propyl or butyl group and a is 0 and b is 0.

This class of surface modifiers is described in U.K. Patent Application No. 9104957.7 filed Mar. 8, 1991 and can be prepared by reacting an appropriate dicarboxylic acid ester with an appropriate monosaccharide amine, preferably in the absence of a solvent, at a reaction temperature from 140° to 200° C.

The surface modifiers are commercially available and/or can be prepared by techniques known in the art. Two or more surface modifiers can be used in combination.

A special class of unconventional anionic wetting agents were found to be especially useful in practicing the present invention. This class of wetting agents include the carboxylate salts, such as sodium and potassium salts of diatrizoic acid, iodipamid, metrizoic acid and the like, which were previously described herein by their chemical names and structures. These agents are components of commercially available drug formulations and have been found to have acceptable safety profiles.

The Microfluidizer

In the practice of the present invention the following microfluidizers were used, all supplied by Microfluidics International Corporation:

Model M110-EH, which is a laboratory scale microfluidizer which utilizes an electric hydraulic pump;

Model M-110Y, which is a laboratory scale microfluidizer equipped with a sanitary pressure transducer connected to a digital data acquisition system;

Model M-140K, which is a high pressure microfluidizer with a pressure limit of 40,000 psi; and Model M-210, which is a pilot plant microfluidizer with a pressure range from 3,000 to 30,000 psi, and with flow rates between 1.9 to 5.7 L/min. It is capable of handling a sample size of 3.8 L or greater.

As indicated, the primary forces attributed to microfluidization by the microfluidizer for producing either emulsions or dispersions, and for reducing mean particle size of water-insoluble materials are:

shear, involving boundary layers, turbulent flow, acceleration and change in flow direction;

impact, involving collision of the particles processed with solid elements of the microfluidizer, and collision between the particles being processed; and cavitation, involving an increased change in velocity with a decreased change in pressure, and turbulent flow.

An additional force can be attributed to attrition, i.e., grinding by friction.

The M-110Y laboratory scale microfluidizer consists of an air motor connected to a hydraulic pump which circulates the process fluid. The formulation stream is propelled at high pressures (up to 23,000 psi) through a specially designed interaction chamber which has fixed microchannels that focus the formulation stream and accelerate it to a high velocity. Within the chamber the formulation is subjected to intense shear, impact and cavitation, all of which contribute to particle size reduction. After processing, the formulation stream is passed through a heat exchanger coil and can be collected or recirculated through the machine. The microfluidizer was typically used in a continuous processing mode for one hour of total processing time. The heat exchanger and interaction chamber were externally cooled with a refrigerated circulating water bath.

The use of microfluidization in pharmaceutical dosage form development has largely been limited to processing of emulsions or liposomes as previously discussed.

The Process of Making the Nanoparticulates

A general procedure for preparing the particles useful in the practice of this invention follows. The x-ray contrast agent selected is obtained commercially and/or prepared by techniques known in the art as described above, in a conventional coarse form. It is preferred, but not essential, that the particle size of the coarse x-ray contrast agent selected be less than about 100 μm, as determined by sieve analysis. If the coarse particle size of the contrast agent is greater than about 100 μm then it is preferred that the coarse particles of the contrast agent be reduced in size to less than 100 μm using a conventional milling method such as airjet or fragmentation milling.

The coarse imaging agent selected can then be added to a liquid medium in which it is essentially insoluble to form a premix. The concentration of the agent in the liquid medium can vary from about 0.1–60% w/w, and preferably is from 5–30% (w/w). It is preferred, but not essential, that the surface modifier be present in the premix. The concentration of the surface modifier can vary from about 0.1 to 90%, and preferably is 1–75%, more preferably 20–60%, by weight based on the total combined weight of the drug substance and surface modifier. The apparent viscosity of the premix suspension is preferably less than about 1000 centipoise.

The premix then can be transferred to the microfluidizer and circulated continuously first at low pressures, then at maximum capacity having a fluid pressure of from about 3,000 to 30,000 psi until the desired particle size reduction is achieved. The particles must be reduced in size at a temperature which does not significantly degrade the imaging agent. Processing temperatures of less than about 30°–40° C. are preferred.

There are two methods to collect a slurry and re-pass it in a microfluidizer. The "discreet pass" method collects every pass through the microfluidizer until all of the slurry has been passed through before re-introducing it again to the microfluidizer. This guarantees that every substance or particle has "seen" the interaction chamber the same amount of times. The second method recirculates the slurry by collecting it in a receiving tank and allowing the entire mixture to randomly mix and pass through the interaction chamber. We have found that recirculating a slurry is just as effective as the "discreet pass" method, however, maintaining slurry homogeneity in the receiving tank is important.

As used herein, particle size refers to a weight average particle size of less than about 400 nm as measured by conventional particle size measuring techniques well known to those skilled in the art, such as sedimentation field flow fractionation, photon correlation spectroscopy, or disk centrifugation. By "a weight average particle size of less than about 400 nm" it is meant that at least 90% of the particles have a weight average particle size of less than about 400 nm when measured by the above-noted techniques. In preferred embodiments of the invention, the effective average particle size is less than about 250 nm. In some embodiments of the invention, an effective average particle size of less than about 200 nm has been achieved. With reference to the effective average particle size, it is preferred that at least 95% and, more preferably, 99% of the particles have a particle size less than the effective average, e.g., 400 nm. In particularly preferred embodiments, essentially all of the particles have a size less than 400 nm.

The x-ray contrast compositions of this invention comprise the above-described particles and a carrier therefor. For example, the particles can be dispersed in an aqueous liquid which serves as the carrier for the x-ray contrast agent. Other suitable carriers include liquid carriers such as mixed aqueous and nonaqueous solvents, for example water and alcohols, and suitable nonaqueous solvents, such as alcohol; gels; gases, such as air; and powders. The x-ray contrast composition can comprise from about 1–99.9, preferably 2–45 and more preferably 10–25% by weight of the above-described particles, the remainder of the composition being the carrier, additives and the like. Compositions up to about 100% by weight of the particles are contemplated when the composition is in a lyophilized form.

The dose of the contrast agent to be administered can be selected according to techniques known to those skilled in the art such that a sufficient contrast enhancing effect is obtained. Typical doses can range from 50 to 350 mg of iodine per kilogram of body weight of the subject for many imaging applications. For some applications, e.g., lymphography, lower doses, e.g., 0.5–20 mgI/kg, can be effective.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject in need of an x-ray an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a conventional manner. Alternatively, the image pattern can be observed directly on an x-ray sensitive phosphor screen-silver halide photographic film combination.

The compositions of this invention can be administered by a variety of routes depending on the type of procedure and the anatomical orientation of the tissue being examined. Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like.

Illustrative examples of compounds microfluidized in the presence of surface active agents and mean particle size of the microfluidized compounds are shown in Table I.

TABLE I

| Microfluidization of Diagnostic Imaging Agents | | |
|---|---|---|
| Compound % w/w | Surfactant % w/w | Mean Particle Size |
| WIN 70146 (25%) | DOSS (0.33%) | 242 nm (30 min) |
| | | 207 nm (60 min) |
| WIN 70146 (25%) | DOSS (0.33%) | 290 nm (15 min) |
| | | 246 nm (165 min) |
| WIN 70146 (25%) | F108 (6.67%) | 315 nm (15 min) |
| | | 293 nm (75 min) |

TABLE I-continued

Microfluidization of Diagnostic Imaging Agents

| Compound % w/w | Surfactant % w/w | Mean Particle Size |
|---|---|---|
| WIN 8883 (15%) | sodium diatrizoate (0.1%) | 235 nm (60 min) 215 nm (180 min) |
| WIN 8883 (15%) | sodium iodipamide (3%) | 184 nm (60 min) 164 nm (170 min) |
| WIN 70146 (15%) | sodium iodipamide (3%) | 334 nm (60 min) 218 nm (180 min) |
| WIN 70177 (15%) | sodium diatrizoate (1%) | 1097 nm (60 min) 445 nm (190 min) |
| WIN 70177 (15%) | sodium iodipamide (3%) | 221 nm (60 min) 190 nm (180 min) | wherein
WIN 8883 = ethyl-3,5-bis(acetylamino)-2,4,6-triiodobenzoate
WIN 70146 = benzoic acid, 3,5-bis(acetylamino)-2,4,6-triiodo-1-(ethoxycarbonyl)pentyl ester
WIN 70177 = propanedioic acid, [[3,5-bis(acetylamino)-2,4,6-triiodobenzoyl]oxy]methyl-, bis(1-methylethyl ester The process of the present invention represents a substantial improvement over media and ball milling in providing nanoparticulate drug formulations. The results of experiments show that microfluidization can be used to reduce particle size distribution of contrast agent in a very short period of time, without causing unacceptable decomposition of the drug substance or excipients. Further, the process introduces little or no contamination in the form of trace metals and therefore may be especially well-suited for use in the preparation of nanoparticulate parenteral products in general.

The invention has been described in detail with particular reference to certain preferred embodiments thereof, but it will be understood that variations and modifications can be effected within the spirit and scope of the invention.

What is claimed is:

1. A process for preparing particles consisting essentially of 99.9–1% by weight of a non-radioactive crystalline organic x-ray contrast agent having a solubility in water of less than 10 mg/ml, said x-ray contrast agent having a surface modifier adsorbed on the surface thereof in an amount of 0.1–90% by weight and sufficient to maintain an average particle size of less than about 400 nm, said process comprises the steps of:
preparing a premix of said x-ray contrast agent and said surface modifier by mixing them; and
subjecting said premix to mechanical means to reduce the particle size thereof to less than 400 nm by the action of said mechanical means which produces shear, impact, cavitation and attrition.

2. The process of claim 1 wherein said particles have an effective particle size of less than 300 nm.

3. The process of claim 1 wherein said particles have an effective particle size of less than 200 nm.

4. The process of claim 1 wherein said x-ray contrast agent is an iodinated aromatic compound.

5. The process of claim 1 wherein said x-ray contrast agent is an ester or an amide of an iodinated aromatic acid selected from the group consisting of diatrizoic acid, metrizoic acid, iothalamic acid, trimesic acid and iodipamide.

6. The process of claim 1 wherein said x-ray contrast agent is ethyl-3,5-diacetamido-2,4,6-triiodobenzoate.

7. The process of claim 1 wherein said x-ray contrast agent is ethyl(3,5-bis(acetylamino)-2,4,6-triiodobenzoyloxy)acetate.

8. The process of claim 1 wherein said x-ray contrast agent is ethyl-2-(3,5-bis(acetylamino)-2,4,6-triiodobenzoyloxy)butyrate.

9. The process of claim 1 wherein said carrier is an aqueous liquid.

10. The process of claim 1 wherein said particles are present in an amount of 10–25% by weight.

11. The process of claim 1 wherein said surface modifier is a tetrafunctional block copolymer derived from sequential addition of propylene oxide and ethylene oxide to ethylenediamine.

12. The process of claim 1 wherein said surface modifier has the formula $$L\begin{matrix}CONCH_2(CHOH)_xCH_2OH \\ | \\ R^1 \\ \\ CONCH_2(CHOH)_yCH_2OH \\ | \\ R^2\end{matrix}$$

wherein $$L \text{ is } R-CH\begin{matrix}(CH_2)_a- \\ \\ (CH_2)_b-\end{matrix}, R-L'-\bigodot, $$

$$R-L'-\bigodot-\bigodot \text{ or } R-L'-\bigodot-\bigodot$$

L' is a chemical bond, —O—, —S—, —NH—, —CONH— or —SO$_2$NH—;

R is a hydrophobic substituted or unsubstituted alkyl, substituted or unsubstituted cycloalkyl, or a substituted or unsubstituted aryl group;

each of R$^1$ and R$^2$ independently is hydrogen or an alkyl group having from 1 to 4 carbon atoms;

each of a and b independently is 0 or an integer from 1 to 3, provided that the sum of a and b is not greater than 3; and each of x and y independently is an integer from 3 to 7.

13. The process of claim 1 wherein said particles consist essentially of crystalline ethyl-3,5-diacetamido- 2,4,6-triiodobenzoate having a tetrafunctional block copolymer derived from sequential addition of ethylene oxide and propylene oxide to ethylenediamine adsorbed on the surface.

14. The process of claim 1 wherein said particles consist essentially of crystals of the ethyl glycolate ester of diatrizoic acid having a tetrafunctional block copolymer derived from sequential addition of ethylene oxide and propylene oxide to ethylenediamine adsorbed on the surface thereof.

15. The process of claim 1 wherein said particles consist essentially of crystalline ethyl-2-(3,5-bis(acetylamino)- 2,4,6-triiodobenzoyloxy)butyrate having a tetrafunctional block copolymer derived from sequential addition of ethylene oxide and propylene oxide to ethylenediamine adsorbed on the surface thereof.

16. The process of claim 1 wherein said surface modifier is a carboxylate salt of a compound of the formula A 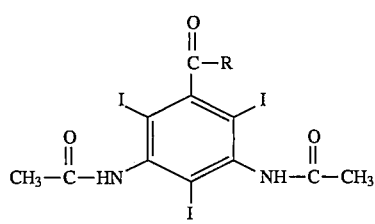
[diatrizoate]

B 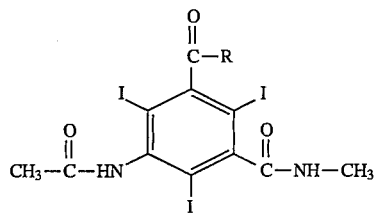
[iothalamate]

C 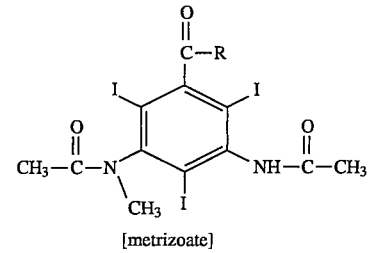
[metrizoate]

D 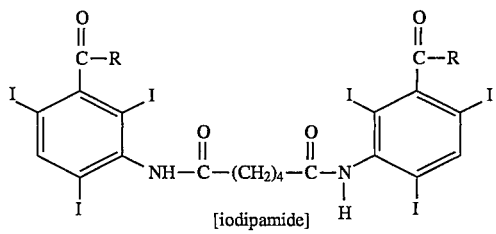
[iodipamide]

-continued

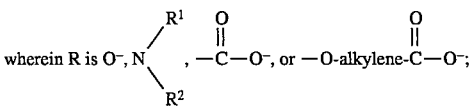

wherein $R^1$ or $R^2$ or both contain anionic carboxylate functionalities.

17. The process of claim 16 wherein the alkylene group contains from 1 to 4 carbons.

18. The process of claim 16 wherein said carboxylate salt is a sodium salt.

19. The process of claim 16 wherein said carboxylate salt is a potassium salt.

20. A method for medical x-ray diagnostic imaging which comprises administering to the body of a test subject an effective contrast producing amount of the x-ray contrast composition prepared by the process of claim 1.

21. A process for preparing stable, dispersible particles consisting essentially of 99.9–1% by weight of a radiopaque crystalline organic x-ray contrast agent having a solubility in water of less than 10 mg/ml, said x-ray contrast agent having a surface modifier adsorbed on the surface thereof in an amount of 0.1–90% by weight and sufficient to maintain an average particle size of less than about 400 nm, said process comprises the steps of:

preparing a premix of said x-ray contrast agent and said surface modifier by mixing therein; and subjecting said x-ray contrast agent of the premix to a comminuting action of a microfluidizer asserting shear, impact, cavitation and attrition forces for a time necessary to reduce the mean particle size thereof to less than 400 nm.

22. The process of claim 21 wherein the time for subjecting said x-ray contrast agent of the premix to a comminuting action of a microfluidizer is 15 minutes to 180 minutes.

* * * * *